(12) United States Patent
Johnston

(10) Patent No.: US 11,181,515 B2
(45) Date of Patent: Nov. 23, 2021

(54) SCENT-BASED SPOILAGE SENSING REFRIGERATOR

(71) Applicant: Amazon Technologies, Inc., Seattle, WA (US)

(72) Inventor: Simon Kurt Johnston, Bellevue, WA (US)

(73) Assignee: Amazon Technologies, Inc., Seattle, WA (US)

( * ) Notice: Subject to any disclaimer, the term of this patent is extended or adjusted under 35 U.S.C. 154(b) by 452 days.

(21) Appl. No.: 16/443,051

(22) Filed: Jun. 17, 2019

(65) Prior Publication Data

US 2019/0311598 A1 Oct. 10, 2019

Related U.S. Application Data

(62) Division of application No. 15/069,168, filed on Mar. 14, 2016, now Pat. No. 10,373,472.

(51) Int. Cl.
| | | |
|---|---|---|
| *G01N 33/00* | (2006.01) | |
| *G01N 33/02* | (2006.01) | |
| *G08B 21/18* | (2006.01) | |
| *F25D 29/00* | (2006.01) | |
| *F25D 11/00* | (2006.01) | |

(52) U.S. Cl.
CPC ......... *G01N 33/0063* (2013.01); *F25D 11/00* (2013.01); *F25D 29/005* (2013.01); *F25D 29/008* (2013.01); *G01N 33/02* (2013.01); *G08B 21/18* (2013.01); *F25D 2323/021* (2013.01); *F25D 2500/06* (2013.01)

(58) Field of Classification Search
CPC ..... G01N 33/0063; G01N 33/02; G08B 21/18
See application file for complete search history.

(56) References Cited

U.S. PATENT DOCUMENTS

| 10,281,200 B2 * | 5/2019 | Johnston | G06T 7/13 |
|---|---|---|---|
| 10,373,472 B2 * | 8/2019 | Johnston | G01N 33/0063 |
| 2006/0130498 A1 * | 6/2006 | Joshi | F25D 17/042 62/127 |
| 2010/0295435 A1 * | 11/2010 | Kendall | F25D 23/028 312/401 |

(Continued)

FOREIGN PATENT DOCUMENTS

| CN | 105222506 | 1/2016 |
|---|---|---|
| DE | 10060629 | 6/2002 |

(Continued)

OTHER PUBLICATIONS

"Food grading" dated May 2, 2016 https://en.m.wikipedia.org/wiki/Food_grading.

(Continued)

*Primary Examiner* — Natalie Huls
(74) *Attorney, Agent, or Firm* — Thomas | Horstemeyer LLP

(57) ABSTRACT

Disclosed are various embodiments for determining whether food in a refrigerator has spoiled. In one embodiment, a refrigerator includes a compartment that has an interior space configured to contain a food item. A chemical sensor can be mounted within an interior of the refrigerator. The chemical sensor can be configured to at least measure an amount of a chemical related to spoilage of the food item in the compartment.

18 Claims, 9 Drawing Sheets

(56) References Cited

U.S. PATENT DOCUMENTS

| | | | |
|---|---|---|---|
| 2012/0023971 A1* | 2/2012 | Min | F25D 29/00 62/62 |
| 2012/0107191 A1* | 5/2012 | Strahle | G01N 21/78 422/401 |
| 2013/0015753 A1 | 1/2013 | Son et al. | |
| 2013/0047630 A1 | 2/2013 | Lu | |
| 2014/0320647 A1 | 10/2014 | Seo et al. | |
| 2014/0360213 A1 | 12/2014 | Son et al. | |
| 2015/0067554 A1 | 3/2015 | Lee et al. | |
| 2015/0178654 A1 | 6/2015 | Glasgow et al. | |
| 2015/0377791 A1 | 12/2015 | Jung et al. | |
| 2016/0018338 A1* | 1/2016 | Song | G01N 21/783 422/420 |
| 2016/0084569 A1* | 3/2016 | Kocaturk | F25D 17/065 62/337 |
| 2016/0162715 A1* | 6/2016 | Luk | F25D 29/005 235/385 |
| 2016/0203591 A1* | 7/2016 | Justaniah | G06T 7/0004 348/89 |
| 2016/0252297 A1* | 9/2016 | Jeong | F25D 29/006 62/62 |
| 2017/0123389 A1 | 5/2017 | Baez et al. | |
| 2017/0160005 A1* | 6/2017 | Park | F25D 29/005 |
| 2017/0184342 A1* | 6/2017 | Tae | G06K 7/10366 |
| 2017/0219279 A1* | 8/2017 | Chae | F25D 29/005 |
| 2018/0007453 A1* | 1/2018 | Taylor | G01N 33/02 |
| 2020/0000113 A1* | 1/2020 | Eaton | F25D 25/025 |
| 2020/0097776 A1* | 3/2020 | Kim | G06K 9/00771 |

FOREIGN PATENT DOCUMENTS

| | | |
|---|---|---|
| JP | 2001041640 | 2/2001 |
| KR | 20120011486 | 2/2012 |

OTHER PUBLICATIONS

"Food sniffer" dated May 2, 2016 http://www.myfoodsniffer.com/.

Blasco, J., et al. "Recognition and classification of external skin damage in citrus fruits using multispectral data and morphological features." Biosystems engineering 103.2 (2009): 137-145.

Buzby et al. "The Estimated Amount, Value, and Calories of Postharvest Food Losses at the Retail and Consumer Levels in the United States"; USDA, Tech. Report, Feb. 2014.

International Search Report dated Nov. 27, 2017 (PCT/US2017/020094).

Ishimwe et al. "Applications of Thermal Imaging in Agriculture—A Review"; Advances in Remote Sensing, 3:128-140, (2014).

Laguerre et al., "Study of domestic refrigerator temperature and analysis of factors effecting temperature: a French survey", International Journal of Refrigeration, 25 (2002): pp. 653-659.

Manickavasagan et al. "Applications of Thermal Imaging in Agrictulture—A Review"; Canadian Society for Engineering in agricultural, food, and biological systems, 05-002, (2005).

Manickavasagan et al. "Imaging with Electromagnetic Spectrum"; Applications in Food and Agriculture, (2014).

U.S. Appl. No. 15/069,168, filed Mar. 14, 2016, Final Office Action dated Jun. 15, 2018.

U.S. Appl. No. 15/069,168, filed Mar. 14, 2016, Non-Final Office Action dated Oct. 23, 2018.

U.S. Appl. No. 15/069,168, filed Mar. 14, 2016, Non-Final Office Action dated Nov. 27, 2017.

U.S. Appl. No. 15/069,168, filed Mar. 14, 2016, Response to Non-Final Office Action dated Nov. 27, 2017.

U.S. Appl. No. 15/069,168, filed Mar. 14, 2016, Response to Restriction/Election dated Oct. 20, 2017.

U.S. Appl. No. 15/069,168, filed Mar. 14, 2016, Restriction/Election dated Oct. 20, 2017.

U.S. Appl. No. 15/069,200, filed Mar. 14, 2016, Non-Final Office Action dated Jan. 25, 2018.

U.S. Appl. No. 15/069,200, filed Mar. 14, 2016, Notice of Allowance dated Dec. 21, 2018.

U.S. Appl. No. 15/069,200, filed Mar. 14, 2016, Response to Restriction/Election dated Jan. 25, 2018.

U.S. Appl. No. 15/069,200, filed Mar. 14, 2016, Restriction/Election dated Jan. 25, 2018.

Written Opinion dated Nov. 27, 2017 (PCT/US2017/020094).

Yang, Qingsheng, and John A. Marchant. "Accurate blemish detection with active contour models." Computers and electronics in agriculture 14.1 (1996): 77-89.

Zhu, Bin, et al. "30 surface reconstruction of apples from 20 NIR images." Two-and Three-Dimensional Methods for Inspection and Metrology III. vol. 6000. International Society for Optics and Photonics, (2005).

U.S. Appl. No. 15/069,168, filed Mar. 14, 2016, Notice of Allowance dated Mar. 21, 2019.

* cited by examiner

SCENT-BASED SPOILAGE SENSING REFRIGERATOR

CROSS-REFERENCE TO RELATED APPLICATIONS

This application is a divisional of and claims priority to U.S. patent application Ser. No. 15/069,168, entitled "SCENT-BASED SPOILAGE SENSING REFRIGERATOR," filed on Mar. 14, 2016, which is incorporated by reference as if set forth in its entirety herein. This application is related to U.S. patent application Ser. No. 15/069,200, entitled "IMAGE-BASED SPOILAGE SENSING REFRIGERATOR," filed on Mar. 14, 2016, which is incorporated by reference as if set forth in its entirety herein.

BACKGROUND

Although a refrigerator can slow the spoilage of food and drinks stored within the refrigerator, the process is not completely halted. Food or drinks in the refrigerator will eventually spoil. The amount of time required depends on a variety of factors, such as the internal temperature of the refrigerator, where items are located in the refrigerator, whether other items in the refrigerator have begun to spoil, and various other factors. Moreover, a user may not notice that food or drinks within the refrigerator are spoiling because these items may be stored out of sight (e.g., at the back of the refrigerator, in a drawer or bin, or behind another item).

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views.

DETAILED DESCRIPTION

Disclosed are various examples of refrigerators that identify spoiled food and alert a user to the presence of spoiled food. Spoiled food can be detected in a number of ways. For example, chemical sensors located throughout the refrigerator can detect the presence of chemicals generated as a by-product of spoliation. As another example, cameras can be placed through the refrigerator to capture images of food items in the various compartments. In some instances, an infrared camera can be used, while in other instances a visible spectrum camera can be used in addition to or in place of an infrared camera. Images of food captured by a camera can be compared to a model of a spoiled food item in order to identify individual items of food that may be oxidizing; growing mold, mildew, or fungus; rotting; or otherwise spoiling. In the following discussion, a general description of the system and its components is provided, followed by a discussion of the operation of the same.

Figure 1:
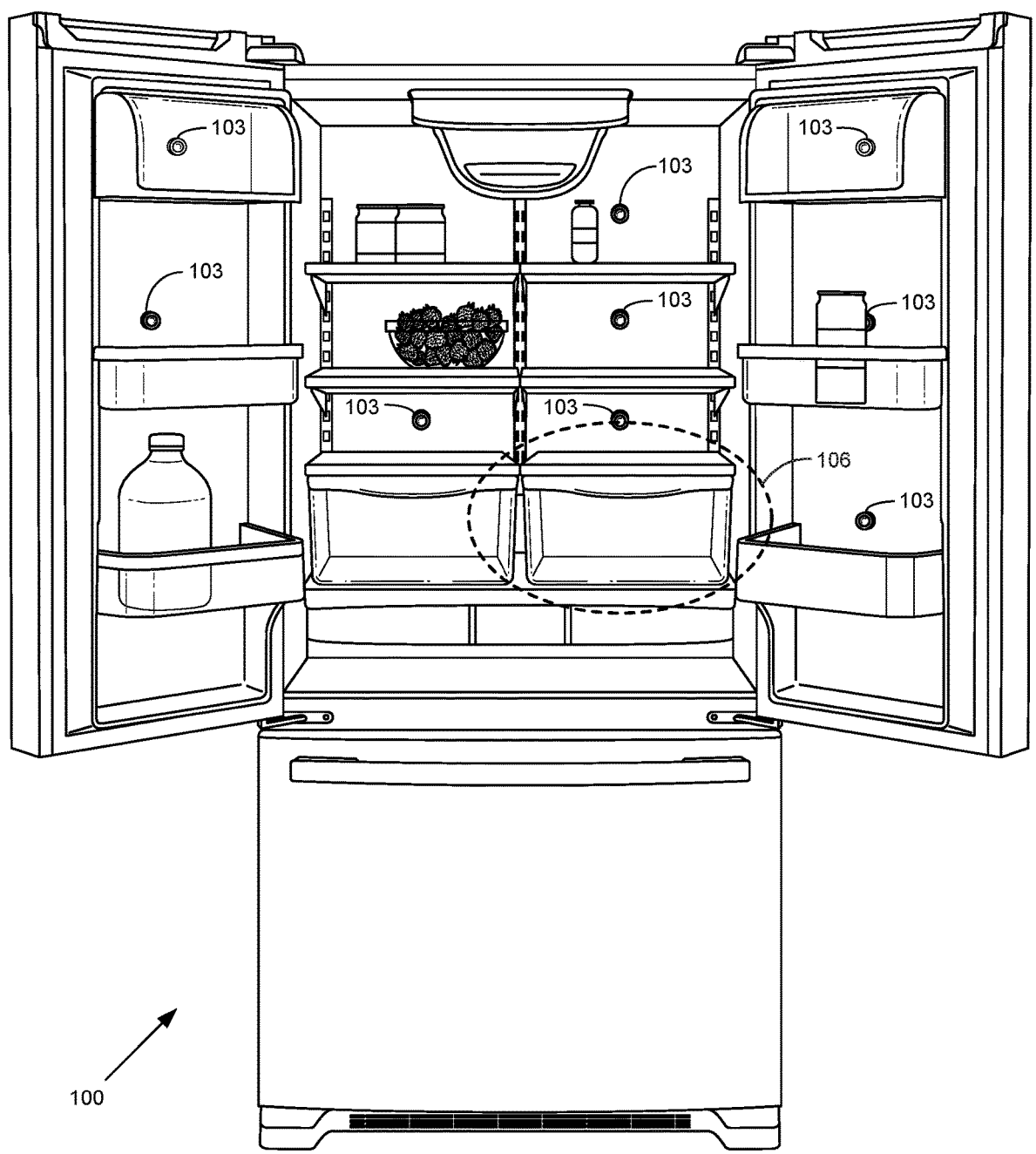
FIG. 1 is a drawing of a refrigerator according to various embodiments of the present disclosure.

Beginning with FIG. 1, a refrigerator 100 is depicted. As illustrated, the refrigerator 100 can include one or more cameras 103. These cameras 103 may be located throughout the refrigerator 100. For example, each compartment 106, such as a shelf, tray, or drawer, can include a camera 103 positioned to capture an image of the corresponding shelf, tray, or compartment 106. In some embodiments, the camera 103 can include an camera 103 capable of capturing images in the infrared spectrum and/or a camera 103 capable of capturing images in the visible spectrum. In other embodiments, the camera 103 can correspond to a complementary metal-oxide-semiconductor (CMOS) sensor capable of capturing both infrared and visible spectrum images.

Figure 2:
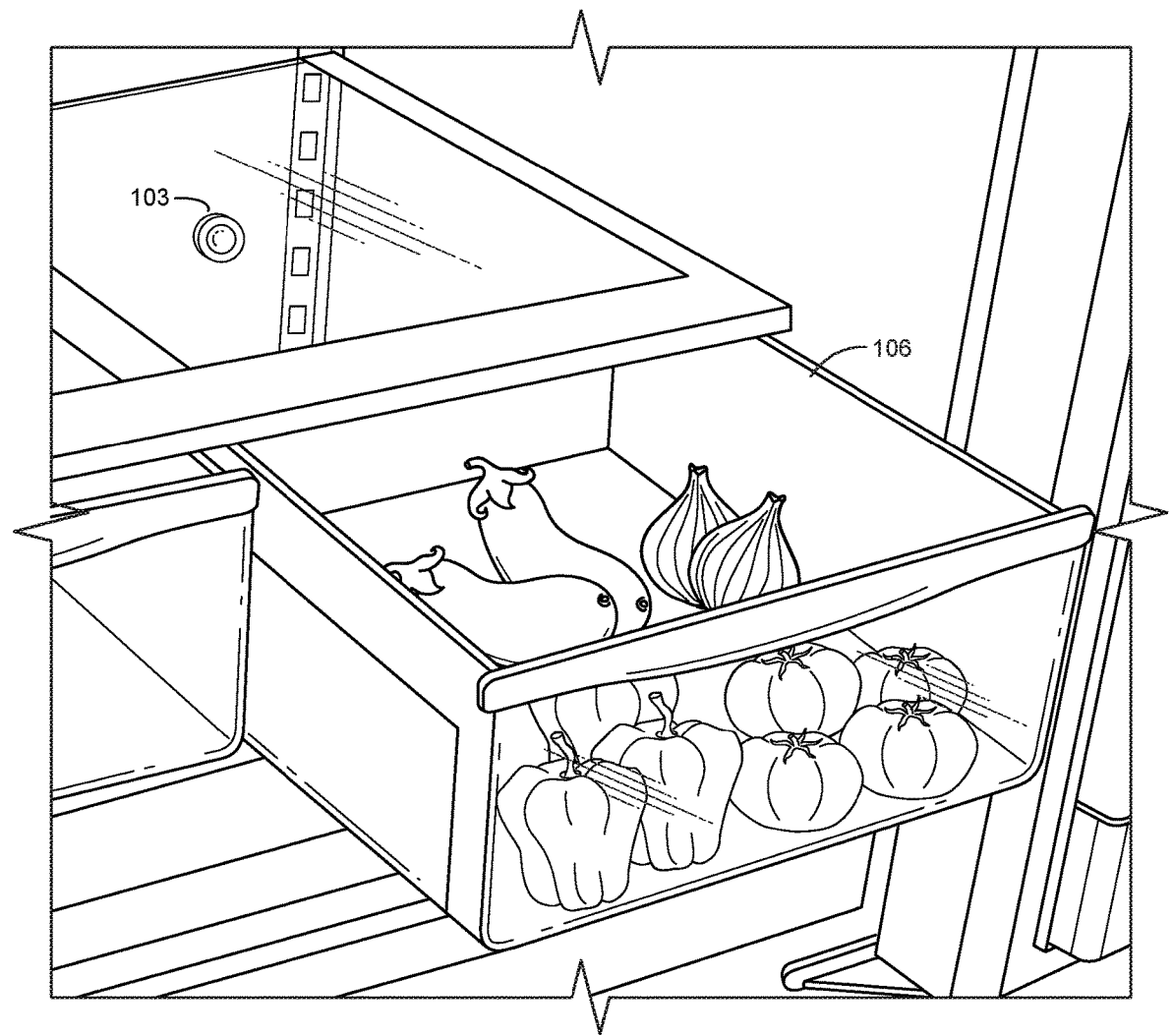
FIG. 2 is a drawing of a portion of the refrigerator depicted in FIG. 1.

Moving on to FIG. 2, shown is a close-up view of a compartment 106 of the refrigerator. In this example, the compartment 106 depicted includes a drawer, such as a crisper, meat drawer, or similar compartment 106. Behind the drawer is a camera 103 placed to capture an image of the compartment 106 and its contents. Due to the placement of the camera 103, an image of the contents of the compartment 106 can be captured by the camera 103.

Although the camera 103 depicted in FIG. 2 is placed behind the drawer, the camera 103 can be placed in other locations. For example, the camera 103 could be placed on the underside of the shelf of the compartment 106. In this example, the camera 103 would be able to capture images without potential interference or distortion from the walls of the compartment 106. The camera 103 can also be placed in other locations in order to capture an image of the compartment 106 from other angles or to capture particular views of the compartment 106.

Figure 3:
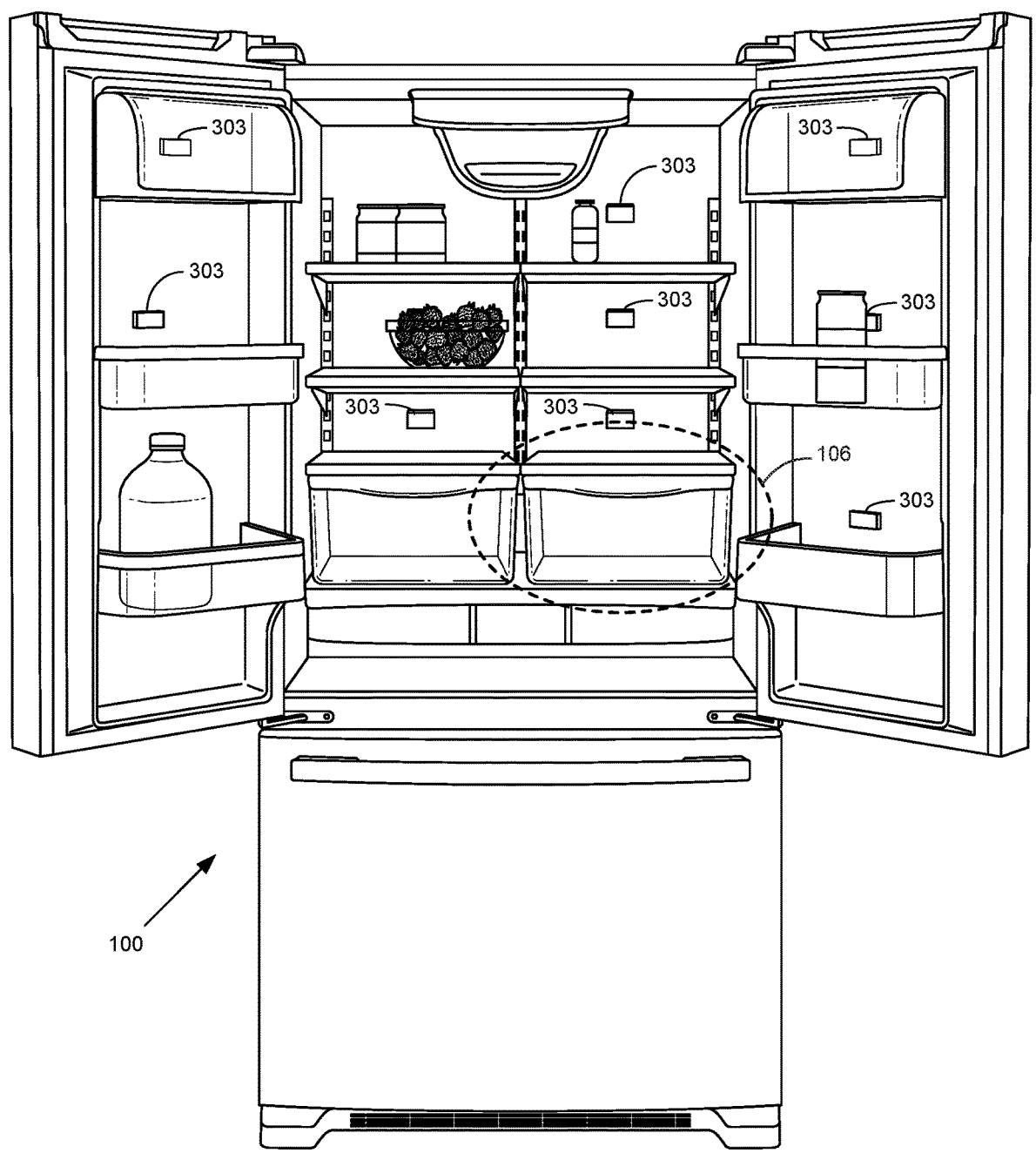
FIG. 3 is a drawing of a refrigerator according to various embodiments of the present disclosure.

Referring next to FIG. 3, a refrigerator 100 is depicted. As illustrated, the refrigerator 100 can include one or more chemical sensors 303. These chemical sensors 303 may be located throughout the refrigerator 100. For example, each compartment 106, such as a shelf, tray, or drawer can include a chemical sensor 303 positioned to detect chemicals generated from spoiling or decomposing food located on the corresponding shelf, tray, or compartment 106. To minimize the false positives or false negatives, the compartments 106 may be positioned in the refrigerator or otherwise configured to minimize or eliminate airflow between compartments 106. For example, each compartment 106 may be connected to a separate spine providing airflow to the compartment instead of being connected to a common spine providing airflow. As another example, each compartment 106 may be connected to a separate exhaust path, minimizing air movement between compartments 106. In some instances, one or more compartments 106 can be fully sealed to prevent air leaking out of compartment 106 into another compartment 106. In some of these instances, the sealed compartment 106 can be provided with an independent supply of air and an independent exhaust system to circulate air through the sealed compartment 106. These various configurations allow for the chemical sensor 303 of the compartment 106 to sample chemicals generated from spoiling or decomposing food in the compartment 106 itself, rather than a neighboring compartment 106.

Figure 4:
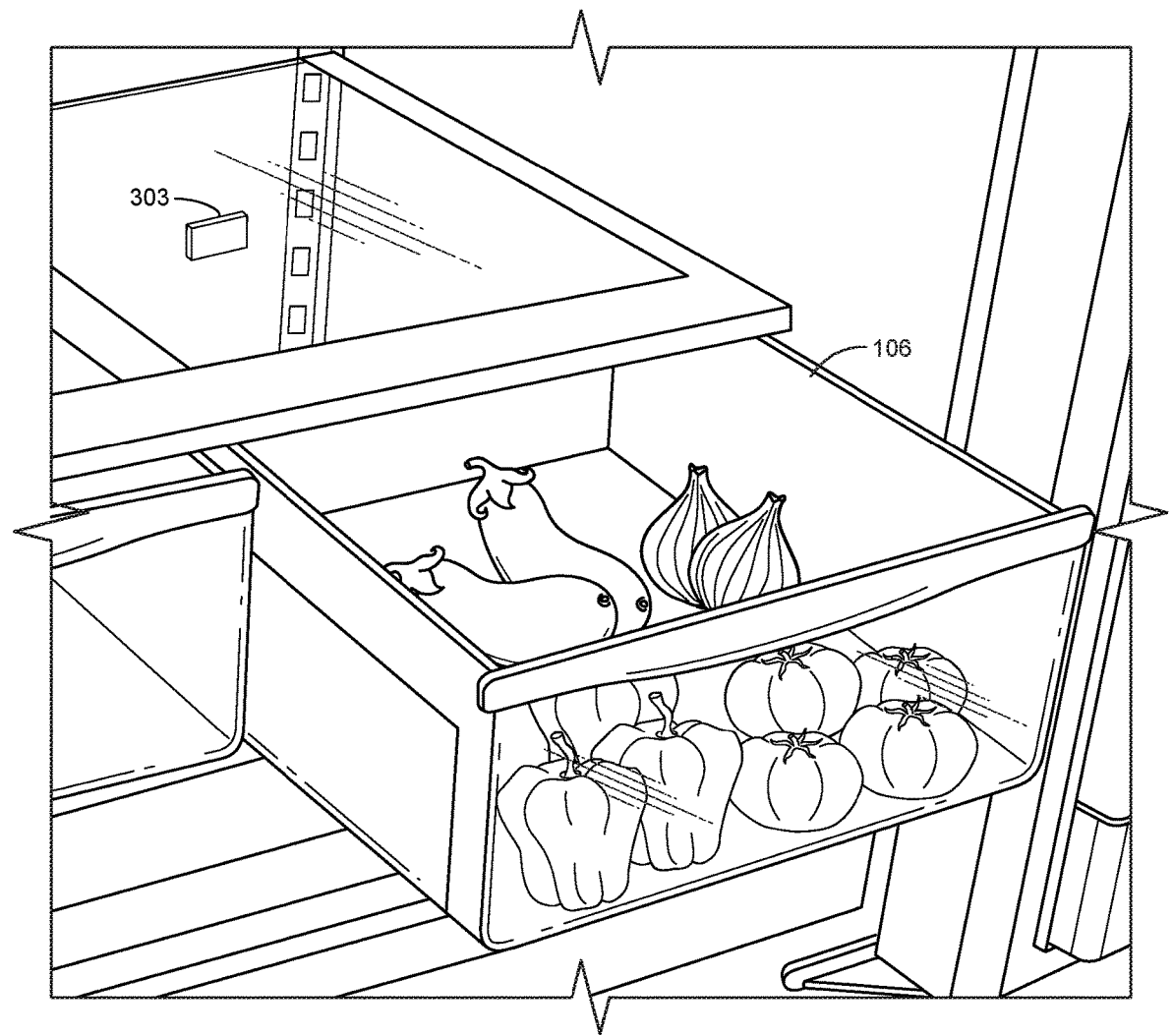
FIG. 4 is a drawing of a portion of the refrigerator depicted in FIG. 3.

Proceeding to FIG. 4, shown is a close-up view of a compartment 106 of the refrigerator. In this example, the compartment 106 depicted includes a drawer, such as a crisper, meat drawer, or similar compartment 106. Behind the drawer is a chemical sensor 303 placed to detect chemicals generated by spoiling or rotting food in the compartment 106.

Figure 5:
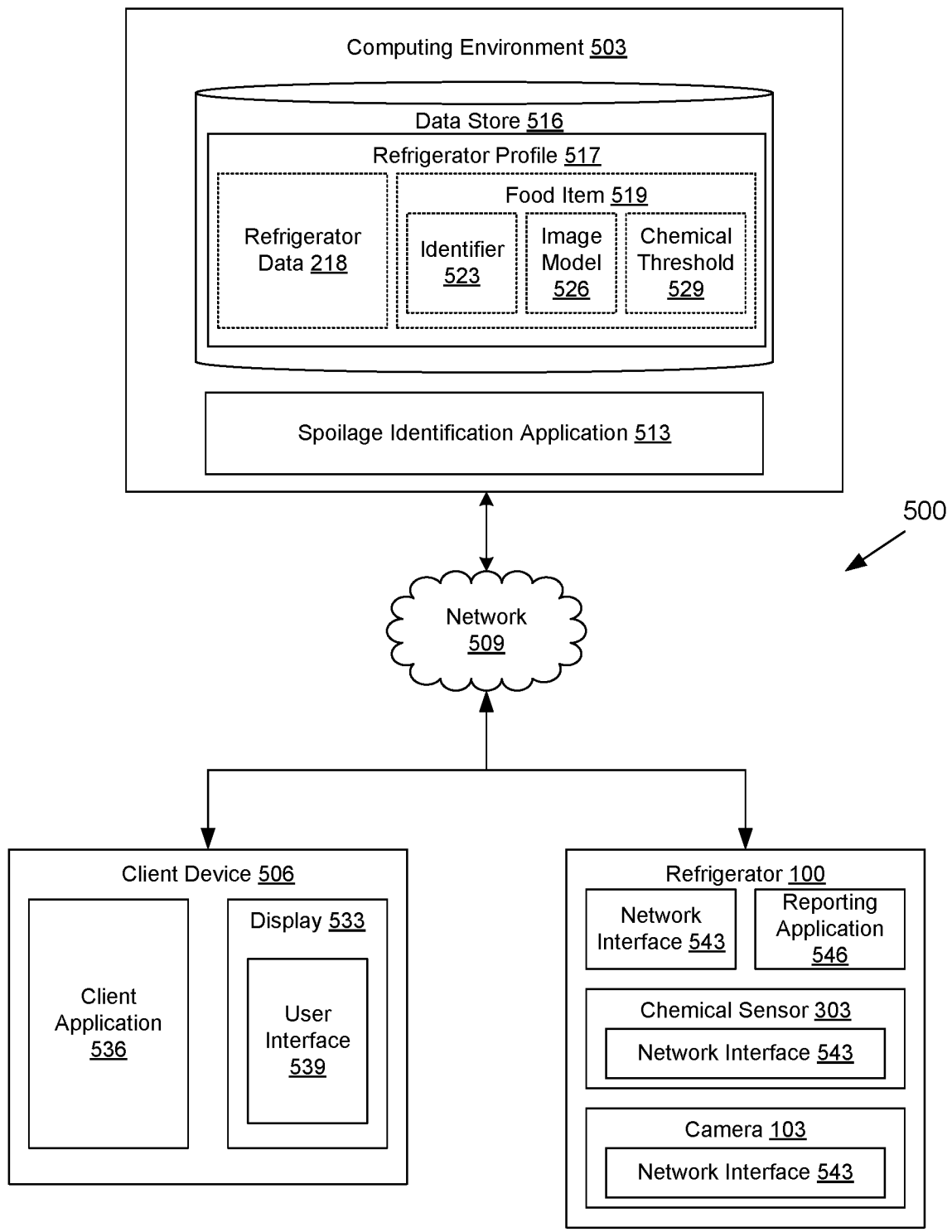
FIG. 5 is a drawing of a networked environment according to various embodiments of the present disclosure.

With reference to FIG. 5, shown is a networked environment 500 according to various embodiments. The networked environment 500 includes a computing environment 503, a client device 506, and a refrigerator 100, which are in data communication with each other via a network 509. The network 509 includes, for example, the Internet, intranets, extranets, wide area networks (WANs), local area networks (LANs), wired networks, wireless networks, or other suitable networks, or any combination of two or more such networks. For example, such networks may comprise satellite networks, cable networks, Ethernet networks, and other types of networks.

The computing environment 503 may include a server computer or any other system providing computing capability. Alternatively, the computing environment 503 may employ a plurality of computing devices that may be arranged in one or more server banks or computer banks or other arrangements. Such computing devices may be located in a single installation or may be distributed among many different geographical locations. For example, the computing environment 503 may include a plurality of computing devices that together may comprise a hosted computing resource, a grid computing resource, or any other distributed computing arrangement. In some cases, the computing environment 503 can correspond to an elastic computing resource where the allotted capacity of processing, network, storage, or other computing-related resources may vary over time.

Various applications or other functionality may be executed in the computing environment 503 according to various embodiments. The components executed on the computing environment 503, for example, include the spoilage identification application 513, and other applications, services, processes, systems, engines, or functionality not discussed in detail herein. The spoilage identification application 513 is executed to determine whether food located in a compartment 106 of a refrigerator 100 has spoiled or is about to spoil, based at least in part on data supplied by the refrigerator 100.

Also, various data is stored in a data store 516 that is accessible to the computing environment 503. The data store 516 may be representative of a plurality of data stores 516 as can be appreciated. The data stored in the data store 516, for example, is associated with the operation of the various applications and/or functional entities described below. The data stored in the data store 516 includes, for example, a refrigerator profile 517 corresponding to the refrigerator 100, and potentially other data.

The refrigerator profile 517 can include refrigerator data 518 for the particular make and model of the refrigerator 518 and a record for each food item 519 stored in the refrigerator. Refrigerator data 518 can include the placement of individual cameras 103 or chemical sensors 303 within a respective refrigerator 100. The refrigerator data 518 can also include data such as an expected volume or rate of airflow within the refrigerator 100 or within a particular compartment 106 of the refrigerator 100. A food item 519 can represent data corresponding to a type or class of food that may be stored in a refrigerator. Each food item 519 can include an identifier 523, an image model 526, a chemical threshold 529, and potentially other data.

The identifier 523 serves as one or more pieces of information that uniquely identifies a food item 519. This can include the type of food item 519, the quantity of the food item 519, and the location of the food item 519 within the refrigerator. For example, the identifier 523 can specify "milk," "half-gallon," and "top-shelf." Likewise, the identifier 523 can specify "onions," "1-dozen," and "crisper drawer."

The image model 526 can represent a model of a spoiled food item 519. For types of food where multiple paths exist for spoliation, multiple image models 526 can be generated. The image model 526 can include a two-dimensional or three-dimensional model of how a spoiled food item 519 might look. For example, if the food item 519 were an apple, then the image model 526 might provide a model or example of what a bruised apple might look like, what a rotting apple might look like, what an apple covered in mold might look like, or what an oxidized apple might look like. For some food items 519, the image model 526 can include a particular color to look for that is indicative of spoiling. The image model 526 can be compared to images captured by a camera 103 of the food item 519 in order to determine whether the food item 519 stored in the refrigerator 100 is spoiled.

Different versions of the image model 526 can also exist for different parts of the electromagnetic spectrum. For example, an image model 526 from the infrared spectrum might include particular temperature gradients or differences that correspond to different types of spoiling. For example, bruises on produce may have a particular, localized area that is a different temperature than the rest of the item of produce. Likewise, areas where mold is growing on food may appear hotter (due to the digestive activity of the mold), than other parts.

The image model 526 can be generated by applying various machine learning and computer vision techniques to a series of images of the spoiled food item 519 in order to create an accurate model for the appearance of a spoiled food item 519. For example, a series of images of bruised apples can be used to form the basis for a model of a bruised apple. Likewise, a series of images of mold growing on apples can be used to form the basis for a model of a rotting apple. Similar approaches can be used to generate image models 526 for other types of food.

The chemical threshold 529 represents a threshold level or quantity of a chemical associated with the spoliation of food that a chemical sensor 303 should detect in order for the spoilage identification application 513 to determine that the food item 519 has spoiled. The chemical threshold 529 can be based on a number of factors, such as the quantity of food items 519 in a compartment 106, the airflow through the compartment 106, the volume of the compartment 106, and potentially other factors. For example, a large number of unspoiled bananas can emit the same quantity of ethylene gas as a single, spoiling banana. Accordingly, the chemical threshold 529 may need to be adjusted as the quantity of bananas changes. Likewise, the airflow through a compartment 106 and the volume of the compartment 106 will affect the rate at which various volatile organic compounds build up within the compartment 106. For example, a large compartment 106 with a high rate of airflow might only accumulate small amounts of volatile organic compounds associated with spoiling food. In such an example, the chemical threshold 529 would need to be set lower than it would for a compartment 106 that were smaller or had less airflow.

The client device 506 is representative of a plurality of client devices that may be coupled to the network 509. The client device 506 can include a processor-based system such as a computer system embodied in the form of a desktop computer, a laptop computer, a personal digital assistant, a cellular telephone, a smartphone, a set-top box, a music player, a web pad, a tablet computer system, a game console, an electronic book reader, or some other device with like capability. The client device 506 can also include a display 533. The display 533 can include one or more devices such as a liquid crystal display (LCD), gas plasma-based flat panel displays, organic light emitting diode (OLED) display, electrophoretic ink (E ink) display, projector, or other display devices.

Although depicted separately, in some instances in FIG. 2, the client device 506 can also include the refrigerator 100. For example, many "smart" refrigerators include network connectivity, a processor capable of executing one or more applications, and a display for providing information to a user. In these instances, the refrigerator 100 can include the functionality of the client device 506.

The client device 506 can be configured to execute various applications such as a client application 536. The client application 536 may be executed by a client device 506 to access network content served up by the computing environment 503 or other servers, thereby rendering a user interface 539 on the display 533. To this end, the client application 536 can include a browser, a dedicated application, etc., and the user interface 539 may include a network page, an application screen, etc. The client device 506 can be configured to execute applications beyond the client application 536 such as email applications, social networking applications, word processors, spreadsheets, games, or other applications.

The refrigerator 100, or the individual cameras 103 or chemical sensors 303 within the refrigerator 100, can also be in data communication with the computing environment 503 via the network 509. For example, the refrigerator 100 can include a network interface 543 that links the refrigerator 100 to the network 509. The refrigerator can also be configured to execute a reporting application 546 and potentially other applications. The refrigerator 100 can also include one or more chemical sensors 303, one or more cameras 103, and potentially other sensors such as scales, door sensors (e.g., to detect when a door is open or closed) or temperature sensors.

The network interface 543 provides a physical link between the refrigerator 100 and the network 509. Examples of network interfaces 543 include wired interfaces (e.g., an RJ-45 jack for accepting unshielded twisted pair (UTP) cables) or wireless interfaces (e.g., a WI-FI®, BLUETOOTH®, ZIGBEE®, or similar interface). In some instances, a refrigerator 100 can have multiple network interfaces 543 in order to provide an option to connect to multiple different types of networks (e.g., a wired interface and a wireless interface).

The reporting application 546 collects data from the various sensors installed on the refrigerator 100 and reports the data to the spoilage identification application 513. For example, the reporting application 546 may cause one or more chemical sensors 303 to take a reading at predefined or preconfigured intervals of time and report the results to the spoilage identification application 513. Similarly, the reporting application 546 may cause one or more cameras 103 to capture an image of a compartment 106 (FIG. 1) at predefined or preconfigured intervals of time and provide the captured images to the spoilage identification application 513.

The chemical sensor 303 corresponds to a sensor configured to detect the presence and quantity of a chemical in the vicinity of the chemical sensor. In the present disclosure, the chemical sensor 303 can be configured to detect the presence of various chemical compounds released as a result of decomposition of food in the refrigerator 100. These chemical compounds may be the result of oxidation, fermentation, rancidification, ripening, or other decomposition processes resulting in spoliation of food. Such chemical compounds can include various volatile organic compounds, such as ethylene (a by-product of ripening), various alcohols (by-product of fermentation), acetic acid (by-product of fermentation or oxidation), various short-chain fatty acids (a by-product of hydrolytic rancidity), various volatile aldehydes and ketones (by products of oxidation and oxidative rancidity), and other volatile organic compounds. Examples of chemical sensors 303 include potentiometric sensors, chemical field-effect transistor (ChemFET) sensors, chemiresistors, chemoreceptors, or other sensors.

Chemical sensors 303 can be further configured in a number of ways. For example, a chemical sensor 303 can be configured to detect a single chemical. In other examples, a chemical sensor 303 can be configured to detect a number of different chemicals. In configurations where a chemical sensor 303 is configured to detect a single chemical, the chemical sensor 303 may be capable of detecting lower concentrations of the chemical than another chemical sensor 303 configured to detect a number of different chemicals.

The camera 103 can include an infrared camera, a visible spectrum camera (i.e., a camera configured to capture an image using light in the visible spectrum), or a combination of the two in a single apparatus. The camera 103 can include various mirrorless cameras (e.g., CMOS image sensors), mirror cameras, and potentially other types of cameras.

In some instances, a sensor such as a camera 103 or a chemical sensor 303 can also include a network interface 543. For example, the sensor could be in data communication with the computing environment 103 through the network interface 543 of the sensor. In these instances, the sensor may communicate directly with the spoilage identification application 513 across the network 509. For example, a camera 103 with a network interface 543 could directly send a captured image to the spoilage identification application 513. As another example, the chemical sensor 303 can directly send a chemical reading to the spoilage identification application 513.

Next, a general description of the operation of the various components of the networked environment 100 is provided. To begin, a user places one or more items of food in the refrigerator 100. In some instances, the user can then use a client application 536 executing on his or her client device 506 to upload information about the current inventory of his or her refrigerator to his or her refrigerator profile 517.

The spoilage identification application 513 can then update individual food items 519 in the refrigerator profile 517 to accurately reflect the addition of extra food to the refrigerator. For example, if there were no milk in the refrigerator 100 previously, the spoilage identification application 513 can create a new food item 519 with an identifier 523 a gallon of milk in response to a user adding a gallon of milk. Likewise, if a user added a half-pound of ground beef to the refrigerator 100, the spoilage identification application 513 can create or update the identifier 523 of a food item 519 record to reflect the new half-pound of beef.

In some embodiments, the reporting application 546 can, at periodic intervals, send sensor readings to the spoilage identification application 513. These periodic intervals may be configured by the user, or communicated to the reporting application 546 by the spoilage identification application 513 based on a variety of factors, such as the internal temperature of the refrigerator 100 or a current airflow of the refrigerator 100 compared to an expected airflow of the refrigerator 100 as indicated in a respective refrigerator profile 517 for the refrigerator 100. These factors can affect the rate at which food spoils and therefore the rate at which sensor readings should be taken and reported. For example, food may spoil more quickly at or near room temperature in comparison to temperatures a few degrees above freezing. Likewise, a blockage in the ventilation system of the refrigerator 100 can result in a reduced airflow, allowing chemicals such as ethylene to accumulate in a compartment 106 and accelerate ripening and spoilage of produce in the compartment 106.

For example, the reporting application 546 can periodically provide a reading from each chemical sensor 303 in the refrigerator 100 to the spoilage identification application 513. Included with each chemical sensor reading 303 is an identification of the location of the chemical sensor 303 (e.g., the compartment 106 in which the chemical sensor 303 is located) As another example, the reporting application 546 can periodically provide an infrared image captured by each camera 103 to the spoilage identification application 513. In some instances, the reporting application 546 can cause a camera 103 to capture a visible spectrum image in response to an even (e.g., the door opening) and provide the captured visible spectrum image to the spoilage identification application 513.

However, in other embodiments, individual sensors such as a camera 103 or chemical sensor 303 can send, at periodic intervals, sensor readings to the spoilage identification application 513. The sensors may be configured by a user to report to the spoilage identification application 513 individual sensor readings. For example, a chemical sensor 303 could be configured to periodically report an amount of a chemical associated with food spoilage to the spoilage identification application 513. As another example, a camera 103 could be configured to periodically capture and provide an image of a corresponding compartment 106 to the spoilage identification application 513.

The spoilage identification application 513 can then use the sensor data received from the reporting application 546 to determine whether an individual food item 519 has spoiled. For example, if a chemical sensor 303 reading is provided, then the spoilage identification application 513 can identify which chemicals and respective quantities are detected. The spoilage identification application 513 can then check the identifiers 523 of individual food items 519 to determine the type and quantity of food item 519 located in the compartment 106 where the chemical sensor 303 is located. The spoilage identification application 513 can then compare the chemical sensor 303 reading to the chemical threshold 529 of each food item 519 located in the compartment 106 to determine whether any food items are spoiled.

Similarly, if an image captured by a camera 103 is provided, then the spoilage identification application 513 can compare the captured image to an image model 526 of a food item 519 stored in the compartment 106. If spoilage identification application 513 determines that the image captured by the camera 103 is sufficiently similar to the image model 526, then the spoilage identification application can determine that one or more items of food in the image had spoiled. For example, if the image model 526 depicts a bruised apple, and the spoilage identification application 513 determines that the surface of an apple in the capture image is covered with a bruise that extends over an area greater than a threshold amount, e.g., a percentage of the visible surface, then the spoilage identification application 513 could determine that the apple is spoiled. For instance, if the threshold were set to 50%, then any image of an apple that indicated bruising over 50% or more of the surface within the view of the camera would be identified as an image of a spoiled apple. Other threshold values can also be used as appropriate for a particular implementation. Likewise, other measures for spoilage can be used as appropriate for various types of food.

In addition, the spoilage identification application 513 can also track changes to a food item 519 by comparing two or more captured images of the food item 519 with each other. As a simple example, the spoilage identification application 513 could determine that an apple in a captured image has a small bruise covering some small percentage of its surface based on a first image captured by a camera 103. In a second image captured by the camera 103 sometime later, the spoilage identification application 513 could determine that the bruise on the apple's surface has become larger and is covering a significant portion of the apple's surface. Based on the change, the spoilage identification application 513 could determine that the apple is spoiling and should be discarded. However, if no change is detected, the spoilage identification application 513 could determine that the apple is still shelf stable and safe to consume.

If the spoilage identification application 513 determines that food in the refrigerator 100 has spoiled, the spoilage identification application 513 can then notify the user. For example, the spoilage identification application 513 can send an electronic notification to the client application 536 to cause the client application 536 to render an alert in the user interface 539 on the client device 506. In some instances, the spoilage identification application 513 can identify the particular food item 519 that has spoiled, or the compartment, drawer or bin within which the food item is stored. In some of these instances, the spoilage identification application 513 can include a copy of an image of the spoiled food taken by a camera 103. In such instances, the spoilage identification application 513 can further highlight the food item 519 to make clear to the user which food item 519 has spoiled.

In some instances, however, the spoilage identification application 513 can be executed locally on the refrigerator 100. In these embodiments, the refrigerator 100 would not have to be in network communication with the computing environment 503 in order to identified spoiled food within the refrigerator 100. For example, if the spoilage identification application 513 were executed on the refrigerator 100, the refrigerator 100 could process readings from individual chemical sensors 303 locally and send an alert, if necessary, to the client device 506. Likewise, the spoilage identification application 513 could perform image analysis on the refrigerator 100 in order to determine whether an item of food has spoiled. For example, certain image analysis approaches may not be computationally intensive and therefore suitable for embedded processors. In these examples, the spoilage identification application 513 may be executed on the refrigerator 100. However, other image analysis approaches may require intensive use of a processor and therefore be unsuitable for an embedded processor. In these examples, the spoilage identification application 513 could be executed on the computing environment 503 in order to have access to additional computational resources (e.g., faster processors, more memory, etc.) beyond those included in the refrigerator 100.

Figure 6:
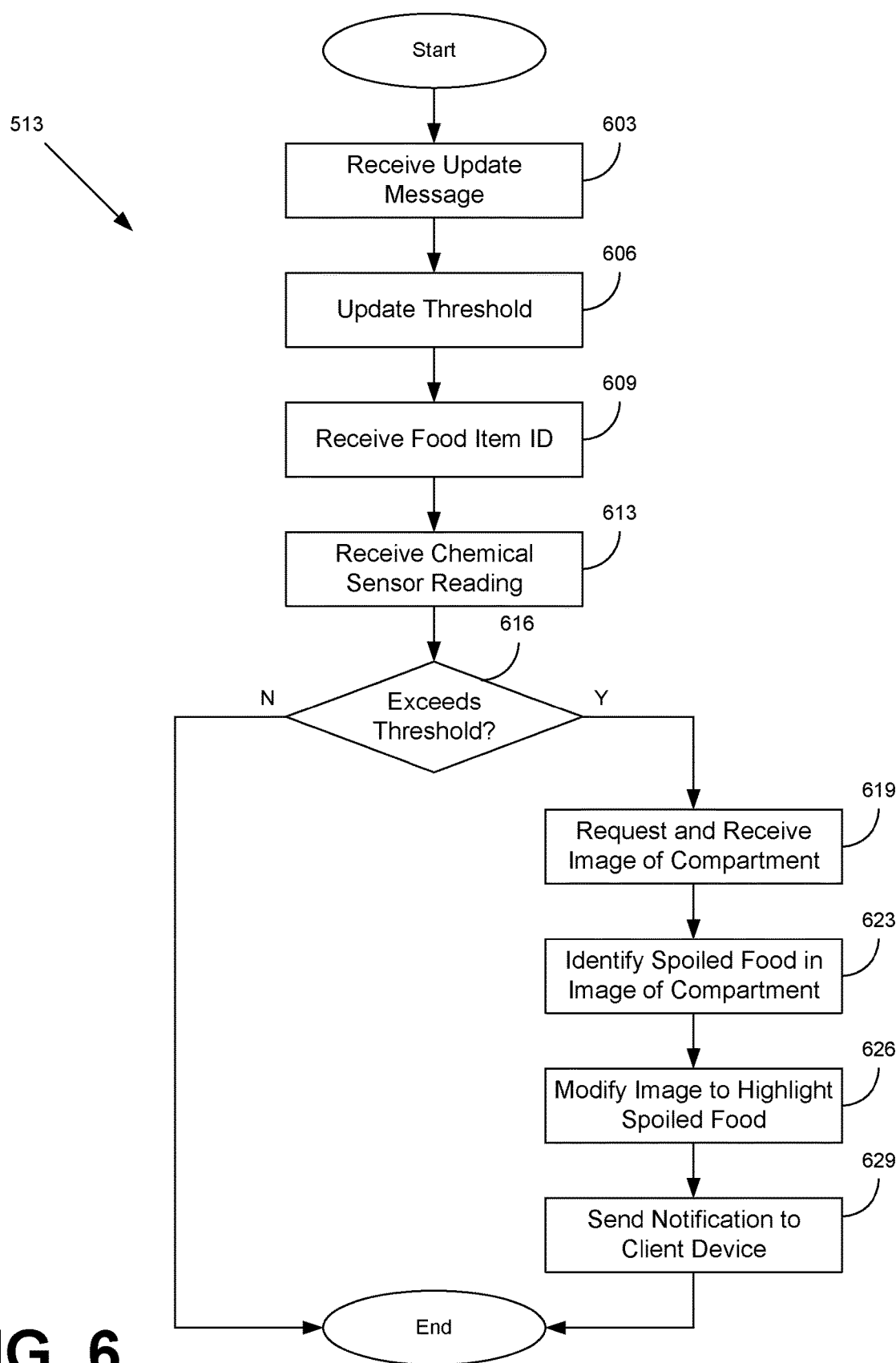
FIG. 6 is a flowchart illustrating one example of functionality implemented as portions of an application executed in the networked environment of FIG. 5 according to various embodiments of the present disclosure.

Referring next to FIG. 6, shown is a flowchart that provides one example of the operation of a portion of the spoilage identification application 513 according to various embodiments. It is understood that the flowchart of FIG. 6 provides merely an example of the many different types of functional arrangements that may be employed to implement the operation of the portion of the spoilage identification application 513 as described herein. As an alternative, the flowchart of FIG. 6 may be viewed as depicting an example of elements of a method implemented in the computing environment 503 (FIG. 5) according to one or more embodiments. In some embodiments, however, the functions of the spoilage identification application 513 described in FIG. 6 can be executed by the refrigerator 100.

Beginning with box 603, the spoilage identification application 513 receives an update message. The update message can contain information regarding the quantity of a food item 519 (FIG. 5) in a compartment 106 (FIG. 3) of the refrigerator 100 (FIG. 3). The update message can be provided from one or more sources.

In some instances, the update message can be provided by the client application 536 (FIG. 5) executing on the client device 506. For example, after a user placed additional food items 519 into the compartment 106, the user can use the client application 536 to update the quantity of food items 519. Likewise, after a user removed a food item 519 from the refrigerator 100, the user can use the client application 536 to update the quantity of food 519.

In other instances, the update message can be provided by the reporting application 546 (FIG. 5) executing on the refrigerator 100. For example, a scale or similar sensor in the compartment 106 can detect a change in weight and the reporting application 546 can report this change to the spoilage identification application 513. If only a single type of food item 519 were stored in the compartment 106, then the change in weight can provide an approximation for changes in the quantity of food items 519 stored in the compartment 106. As a further example, a camera 103 (FIG. 5) could capture an image of the compartment 106 and include the image in the update message. The spoilage identification application 513 could then use various computer vision techniques to identify the food items 519 in the image and compare the identified food items 519 with a previous list of identified food items 519 for the compartment 106 to determine which food items 519 had been added or removed.

Proceeding to box 606, the spoilage identification application 513 updates the chemical threshold 529 (FIG. 5) for the food item 519 stored in the compartment 106. If the quantity of the food item 519 is less, as indicated in the update message, then the spoilage identification application 513 can lower the chemical threshold 529 to a level appropriate for the lesser quantity. Likewise, if the quantity of the food item 519 has increased, the spoilage identification application 513 can increase the chemical threshold 529 to a level that is appropriate for the increased quantity.

Moving on to box 609, the spoilage identification application 513 receives an identifier 523 of a food item 519 from the reporting application 546. The identifier 523 can include the location within the refrigerator 100 (e.g., an identification of a compartment 106) and the type of food item 519 to be evaluated. Referring next to box 613, the spoilage identification application 513 receives a sensor reading captured by a chemical sensor 303 (FIG. 3) in the refrigerator 100.

Proceeding to box 616, the spoilage identification application 513 determines whether the sensor reading reported by the chemical sensor 303 exceeds the chemical threshold 529 established for the food item 519. If the sensor reading does not exceed the chemical threshold 529, then the process ends. However, if the sensor reading does exceed the chemical threshold 529, then the process continues to box 619.

At box 619, the spoilage identification application 513 can send a request to the reporting application 546 for an image of the compartment 106. In response to the request, the spoilage identification application 513 can receive an image of the compartment 106 captured by a camera 103 located within the refrigerator 100. In some instances, the refrigerator 100 can use an infrared camera 103 to immediately capture the image and provide it to the spoilage identification application 513. In other instances, the reporting application 546 can wait until the door of the refrigerator 100 is opened in order to capture a visible spectrum image of the compartment 106 using a visible spectrum camera 103.

Referring next to box 623, the spoilage identification application 513 can identify the spoiled food item 519 in the image of the compartment 106. For example, the spoilage identification application 513 can use various edge-detection, blob detection, or similar computer vision techniques to identify individual food items 519 in the image provided by the reporting application 546. The spoilage identification application 513 can then compare each identified food item 519 with a corresponding image model 526 to determine whether the identified food item 519 has spoiled.

Proceeding to box 626, the spoilage identification application 513 can modify the image to highlight the spoiled food item 519. For example, the spoilage identification application 513 may shade a spoiled food item 519 in the image with a particular color or may draw a box around the spoiled food item 519. The color or box would allow for a user to easily identify the spoiled food item 519 in the image.

Moving on to box 629, the spoilage identification application 513 sends a notification to the client device 506. The notification can include a notice that food in the refrigerator 100 is spoiling. The notification can also include the location (e.g., a particular compartment 106) and type of food that has spoiled. For example, the notification might specify that the apples in the crisper drawer have spoiled. In some instances, the notification can also include a copy of the modified image previously generated in box 626 to assist the user in locating the spoiled food in the refrigerator 100.

In some instances, the spoilage identification application 513 can alternatively or additionally send a notification to the refrigerator 100. For example, in embodiments where the refrigerator 100 includes a display screen, the spoilage identification application 513 can sent the notification to the refrigerator 100 for display on the display screen of the refrigerator 100. The notification can include a notice that food in the refrigerator 100 is spoiling. The notification can also include the location (e.g., a particular compartment 106) and type of food that has spoiled. For example, the notification might specify that the apples in the crisper drawer have spoiled. In some instances, the notification can also include a copy of the modified image previously generated in box 626 to assist the user in locating the spoiled food in the refrigerator 100. After the notification is sent, the process ends.

Figure 7:
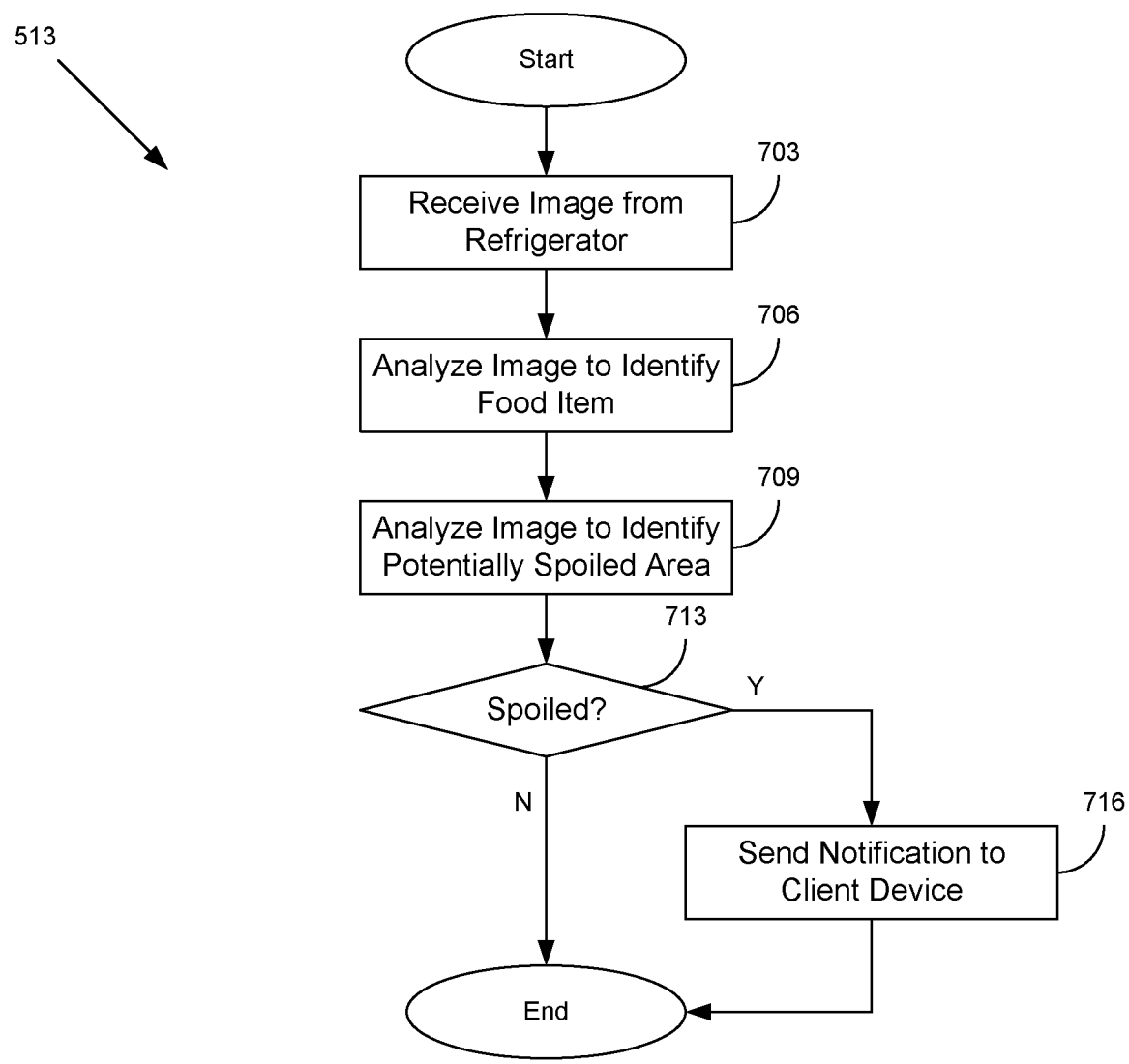
FIG. 7 is a flowchart illustrating one example of functionality implemented as portions of an application executed in the networked environment of FIG. 5 according to various embodiments of the present disclosure.

Referring next to FIG. 7, shown is a flowchart that provides one example of the operation of a portion of the spoilage identification application 513 according to various embodiments. It is understood that the flowchart of FIG. 7 provides merely an example of the many different types of functional arrangements that may be employed to implement the operation of the portion of the spoilage identification application 513 as described herein. As an alternative, the flowchart of FIG. 7 may be viewed as depicting an example of elements of a method implemented in the computing environment 503 (FIG. 5) according to one or more embodiments. In some embodiments, however, the functions of the spoilage identification application 513 described in FIG. 7 can be executed by the refrigerator 100.

Beginning with box 703, the spoilage identification application 513 receives an image of a compartment 106 from the refrigerator 100 (FIG. 5). The image may correspond to an infrared image captured by an infrared camera 103 (FIG. 1) or to a visible spectrum image captured by a visible spectrum camera 103. Infrared images may be used in order to capture an image without requiring a light source (e.g., turning on a light in the refrigerator 100 or waiting until the refrigerator 100 door is open) or to view spoiling portions of food that would be unseen to the naked eye. For example, bruised produce looks different in the infrared spectrum because bruised areas emit heat in a different manner than unbruised areas. Accordingly, a bruise under the surface of produce can remain unseen to the naked eye, but be detectable in the infrared spectrum.

Proceeding to box 706, the spoilage identification application 513 analyzes the image to identify the food item 519 in the image. For example, the spoilage identification application 513 can use various edge-detection, blob detection, or similar computer vision techniques to identify individual food items 519 in the image. The shapes identified using edge-detection or blob detection can then be compared to shapes of food items 519 in order to determine the type of food in the image (e.g., pears versus apples versus chicken drumsticks, etc.) using various computer vision techniques.

Moving on to box 709, the spoilage identification application 513 analyzes the image to identify a potentially spoiled area of an individual food item. First, the spoilage identification application 513 selects a region of the image identified as representing a food item 519. Then, the spoilage identification application 513 identifies any abnormal features or areas of the region image identified as representing the food item 519.

For example, in an infrared image, the spoilage identification application 513 may select an area of the food item 519 that is brighter or darker than the rest of the food item 519. An area that is emitting more heat than the rest of the food item 519 can, for example, indicate that the food item 519 is undergoing active decomposition as various bacteria or fungi actively digest that portion of the food item 519. Likewise, newly formed bruises on produce, such as a bruise on an apple, can appear darker than the rest of the apple in an infrared image.

As another example, in a visible spectrum image, the spoilage identification application 513 can select an area of the food item 519 that is a different color than the rest of the food item 519. As food decomposes, it can discolor due to a number of factors, such as oxidation, hydrolysis, or the growth of mold or other fungi. Accordingly, an area of a food item 519 that is a different color from neighboring regions of the food item 519 can indicate that the food item 519 is spoiled.

Referring next to box 713, the spoilage identification application 513 determines whether the food item 519 has spoiled. The spoilage identification application 513 compares the region to an image model 526 of the food item 519. If the selected region of the image is similar to the image model 526, then the spoilage identification application 513 can determine that the food item 519 has spoiled. For example, if an infrared image of produce is sufficiently similar to an image model 526 of bruised produce, the spoilage identification application 513 can determine that the produce is bruised. Likewise, if a visible spectrum image of a food item 519 is similar to an image model 526 of mold growing on the food item 519, then the spoilage identification application 513 can determine the food item 519 is spoiled due to the growth of mold. If the food item 519 is determined to be spoiled, then execution proceeds to box 716. Otherwise, execution ends.

Proceeding to box 716, the spoilage identification application 513 sends a notification to the client device 506. The notification can include a notice that food in the refrigerator 100 is spoiling. The notification can also include the location (e.g., a particular compartment 106) and type of food that has spoiled. For example, the notification might specify that the apples in the crisper drawer have spoiled. In some instances, the notification can also include a copy of the image provided by the refrigerator 100 to assist the user in locating the spoiled food in the refrigerator 100. In some instances, the image may be modified to highlight the spoiled food item 519 by, for example, changing the color of the spoiled food item 519 or drawing a box around the spoiled food item 519.

In some instances, the spoilage identification application 513 can alternatively or additionally send a notification to the refrigerator 100. For example, in embodiments where the refrigerator 100 includes a display screen, the spoilage identification application 513 can sent the notification to the refrigerator 100 for display on the display screen of the refrigerator 100. The notification can also include the location (e.g., a particular compartment 106) and type of food that has spoiled. For example, the notification might specify that the apples in the crisper drawer have spoiled. In some instances, the notification can also include a copy of the image provided by the refrigerator 100 to assist the user in locating the spoiled food in the refrigerator 100. In some instances, the image may be modified to highlight the spoiled food item 519 by, for example, changing the color of the spoiled food item 519 or drawing a box around the spoiled food item 519. After the notification is sent, the process ends.

Figure 8:
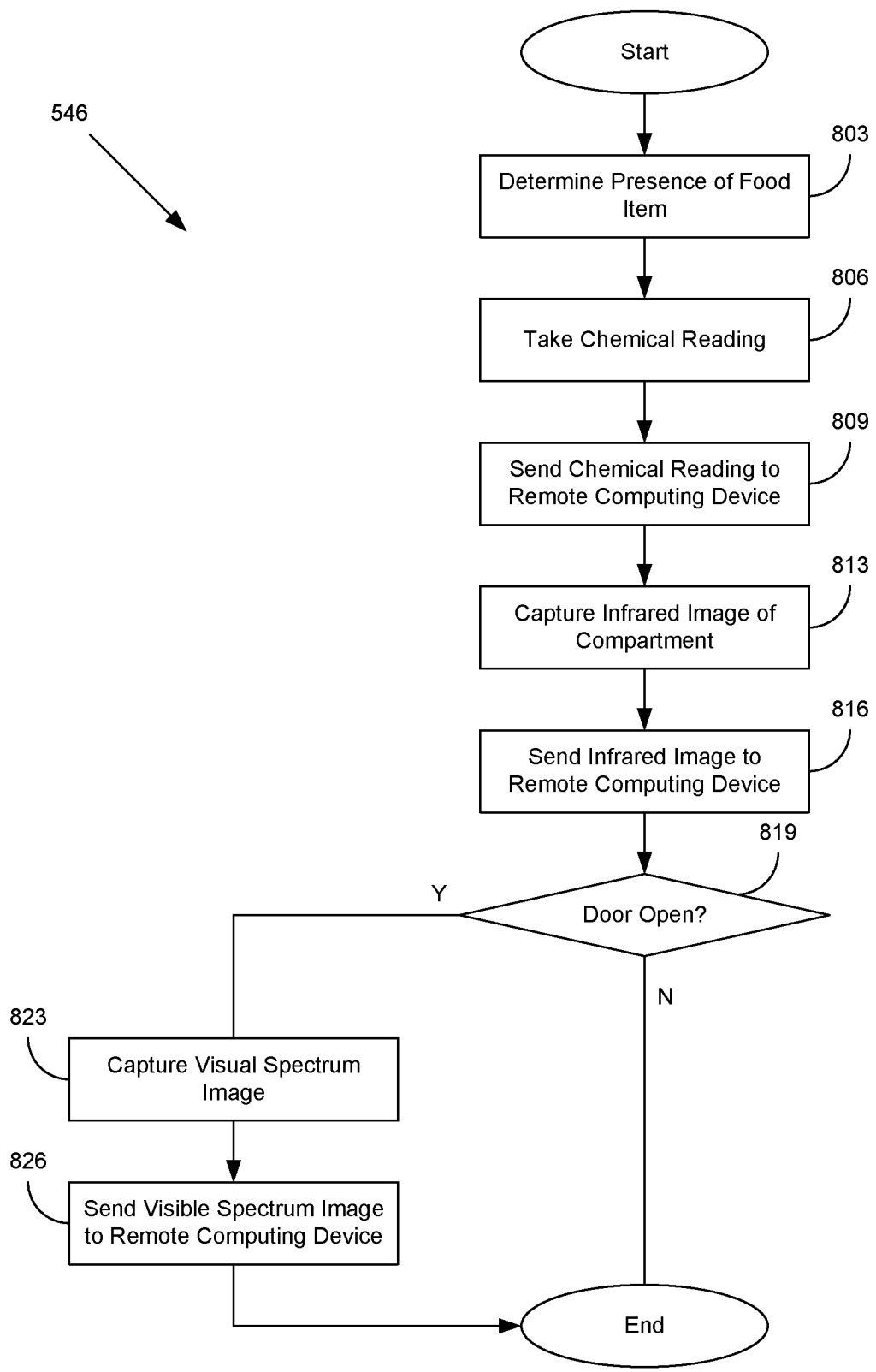
FIG. 8 is a flowchart illustrating one example of functionality implemented as portions of an application executed in the networked environment of FIG. 5 according to various embodiments of the present disclosure.

Referring next to FIG. 8, shown is a flowchart that provides one example of the operation of a portion of the reporting application 546 according to various embodiments. It is understood that the flowchart of FIG. 8 provides merely an example of the many different types of functional arrangements that may be employed to implement the operation of the portion of the reporting application 546 as described herein. As an alternative, the flowchart of FIG. 8 may be viewed as depicting an example of elements of a method implemented by the refrigerator 100 (FIG. 5) according to one or more embodiments.

Beginning with box 803, the reporting application 546 determines whether a food item 519 (FIG. 5) is present in a compartment 106 (FIGS. 1 and 3) of the refrigerator 100 (FIG. 5). For example, the reporting application 546 can read a weight measured by a scale attached to the compartment 106. If the scale is measuring a weight greater than zero, then the reporting application 546 can determine that a food item 519 is present in the compartment.

Proceeding to box 806, the reporting application 546 receives a reading from a chemical sensor 303 (FIG. 3) located in the compartment 106. In some instances, the reporting application 546 causes the chemical sensor 303 to take a reading by sending a query or similar request to the chemical sensor 303. For example, the reporting application 546 can periodically determine whether a food item 519 is present in the compartment 106, as previously described above, and request a reading from the chemical sensor 303 in response to a determination that a food item 519 is located in the compartment 106. In other instances, the chemical sensor 303 can be configured to periodically provide a reading to the reporting application 546.

Moving on to box 809, the reporting application 546 sends the reading from the chemical sensor 303 to a remote computing device. For example, the reporting application 546 can send the reading from the chemical sensor 303 to the spoilage identification application 513 (FIG. 5) executing in the computing environment 503 (FIG. 5).

Referring next to box 813, the reporting application 546 causes an infrared camera 103 to capture an infrared image of the compartment 106. The reporting application 546 can, for example, cause a signal or message to be sent to the infrared camera 103 instructing the infrared camera 103 to capture an infrared image. The infrared camera 103 then returns the captured infrared image to the reporting application 546.

Proceeding to box 816, the reporting application 546 sends the captured infrared image to the remote computing device. For example, the reporting application 546 can send the capture infrared image to the spoilage identification application 513 executing in the computing environment 503.

Moving on to box 819, the reporting application 546 can determine whether a door of the refrigerator 100 has opened. The determination can be made by checking a pressure sensor or magnetic door sensor to determine whether the door is open or closed. If the door is open, and therefore causing the interior of the refrigerator to be illuminated by an internal light or from ambient light in the room, then the reporting application 546 will proceed to box 823 in order to capture a visible spectrum image of the compartment 106. Otherwise, execution ends.

Referring next to box 823, the reporting application 546 causes a visible spectrum camera 103 to capture an infrared image of the compartment 106. The reporting application 546 can, for example, cause a signal or message to be sent to the visible spectrum camera 103 instructing the visible spectrum camera 103 to capture a visible spectrum image. The visible spectrum camera 103 then returns the captured visible spectrum image to the reporting application 546.

Proceeding to box 826, the reporting application 546 sends the captured visible spectrum image to the remote computing device. For example, the reporting application 546 can send the capture infrared image to the spoilage identification application 513 executing in the computing environment 503. After sending the captured visible spectrum image to the remote computing device, execution of the process ends.

Figure 9:
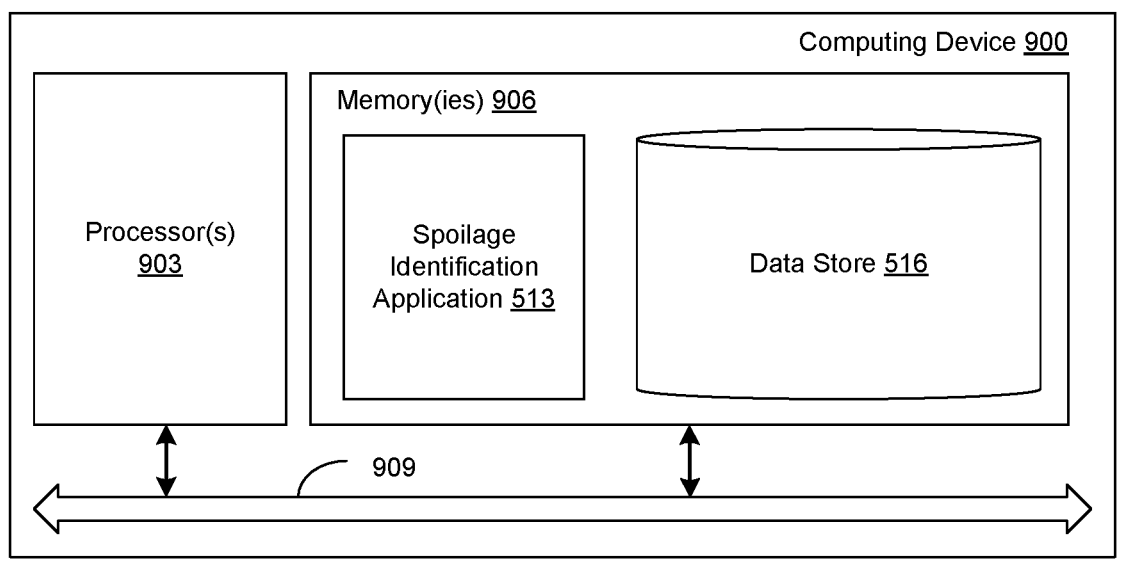
FIG. 9 is a schematic block diagram that provides one example illustration of a computing environment employed in the networked environment of FIG. 1 according to various embodiments of the present disclosure.

With reference to FIG. 9, shown is a schematic block diagram of the computing environment 503 according to an embodiment of the present disclosure. The computing environment 503 includes one or more computing devices 900.

Each computing device 900 includes at least one processor circuit, for example, having a processor 903 and a memory 906, both of which are coupled to a local interface 909. To this end, each computing device 900 may comprise, for example, at least one server computer or like device. The local interface 909 may comprise, for example, a data bus with an accompanying address/control bus or other bus structure as can be appreciated.

Stored in the memory 906 are both data and several components that are executable by the processor 903. In particular, stored in the memory 906 and executable by the processor 903 are the spoilage identification application 513 and potentially other applications. Also stored in the memory 906 may be a data store 516 and other data. In addition, an operating system may be stored in the memory 906 and executable by the processor 903.

It is understood that there may be other applications that are stored in the memory 906 and are executable by the processor 903 as can be appreciated. Where any component discussed herein is implemented in the form of software, any one of a number of programming languages may be employed such as, for example, C, C++, C #, Objective C, Java®, JavaScript®, Perl, P H P, Visual Basic®, Python®, Ruby, Flash®, or other programming languages.

A number of software components are stored in the memory 906 and are executable by the processor 903. In this respect, the term "executable" means a program file that is in a form that can ultimately be run by the processor 903. Examples of executable programs may be, for example, a compiled program that can be translated into machine code in a format that can be loaded into a random access portion of the memory 906 and run by the processor 903, source code that may be expressed in proper format such as object code that is capable of being loaded into a random access portion of the memory 906 and executed by the processor 903, or source code that may be interpreted by another executable program to generate instructions in a random access portion of the memory 906 to be executed by the processor 903, etc. An executable program may be stored in any portion or component of the memory 906 including, for example, random access memory (RAM), read-only memory (ROM), hard drive, solid-state drive, USB flash drive, memory card, optical disc such as compact disc (CD) or digital versatile disc (DVD), floppy disk, magnetic tape, or other memory components.

The memory 906 is defined herein as including both volatile and nonvolatile memory and data storage components. Volatile components are those that do not retain data values upon loss of power. Nonvolatile components are those that retain data upon a loss of power. Thus, the memory 906 may comprise, for example, random access memory (RAM), read-only memory (ROM), hard disk drives, solid-state drives, USB flash drives, memory cards accessed via a memory card reader, floppy disks accessed via an associated floppy disk drive, optical discs accessed via an optical disc drive, magnetic tapes accessed via an appropriate tape drive, and/or other memory components, or a combination of any two or more of these memory components. In addition, the RAM may comprise, for example, static random access memory (SRAM), dynamic random access memory (DRAM), or magnetic random access memory (MRAM) and other such devices. The ROM may comprise, for example, a programmable read-only memory (PROM), an erasable programmable read-only memory (EPROM), an electrically erasable programmable read-only memory (EEPROM), or other like memory device.

Also, the processor 903 may represent multiple processors 903 and/or multiple processor cores and the memory 906 may represent multiple memories 906 that operate in parallel processing circuits, respectively. In such a case, the local interface 909 may be an appropriate network that facilitates communication between any two of the multiple processors 903, between any processor 903 and any of the memories 906, or between any two of the memories 906, etc. The local interface 909 may comprise additional systems designed to coordinate this communication, including, for example, performing load balancing. The processor 903 may be of electrical or of some other available construction.

Although the spoilage identification application 513, the reporting application 546, and other various systems described herein may be embodied in software or code executed by general purpose hardware as discussed above, as an alternative the same may also be embodied in dedicated hardware or a combination of software/general purpose hardware and dedicated hardware. If embodied in dedicated hardware, each can be implemented as a circuit or state machine that employs any one of or a combination of a number of technologies. These technologies may include, but are not limited to, discrete logic circuits having logic gates for implementing various logic functions upon an application of one or more data signals, application specific integrated circuits (ASICs) having appropriate logic gates, field-programmable gate arrays (FPGAs), or other components, etc. Such technologies are generally well known by those skilled in the art and, consequently, are not described in detail herein.

The flowcharts of FIGS. 6, 7, and 8 show the functionality and operation of an implementation of portions of the spoilage identification application 513 and the reporting application 546. If embodied in software, each block may represent a module, segment, or portion of code that comprises program instructions to implement the specified logical function(s). The program instructions may be embodied in the form of source code that comprises human-readable statements written in a programming language or machine code that comprises numerical instructions recognizable by a suitable execution system such as a processor 903 in a computer system or other system. The machine code may be converted from the source code, etc. If embodied in hardware, each block may represent a circuit or a number of interconnected circuits to implement the specified logical function(s).

Although the flowcharts of FIGS. 6, 7, and 8 show a specific order of execution, it is understood that the order of execution may differ from that which is depicted. For example, the order of execution of two or more blocks may be scrambled relative to the order shown. Also, two or more blocks shown in succession in FIGS. 6, 7, and 8 may be executed concurrently or with partial concurrence. Further, in some embodiments, one or more of the blocks shown in FIGS. 6, 7, and 8 may be skipped or omitted. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein, including the spoilage identification application 513 and the reporting application 546, that comprises software or code can be embodied in any non-transitory computer-readable medium for use by or in connection with an instruction execution system such as, for example, a processor 903 in a computer system or other system. In this sense, the logic may comprise, for example, statements including instructions and declarations that can be fetched from the computer-readable medium and executed by the instruction execution system. In the context of the present disclosure, a "computer-readable medium" can be any medium that can contain, store, or maintain the logic or application described herein for use by or in connection with the instruction execution system.

The computer-readable medium can comprise any one of many physical media such as, for example, magnetic, optical, or semiconductor media. More specific examples of a suitable computer-readable medium would include, but are not limited to, magnetic tapes, magnetic floppy diskettes, magnetic hard drives, memory cards, solid-state drives, USB flash drives, or optical discs. Also, the computer-readable medium may be a random access memory (RAM) including, for example, static random access memory (SRAM) and dynamic random access memory (DRAM), or magnetic random access memory (MRAM). In addition, the computer-readable medium may be a read-only memory (ROM), a programmable read-only memory (PROM), an erasable programmable read-only memory (EPROM), an electrically erasable programmable read-only memory (EEPROM), or other type of memory device.

Further, any logic or application described herein, including the spoilage identification application 513 and the reporting application 546, may be implemented and structured in a variety of ways. For example, one or more applications described may be implemented as modules or components of a single application. Further, one or more applications described herein may be executed in shared or separate computing devices or a combination thereof. For example, a plurality of the applications described herein may execute in the same computing device 900, or in multiple computing devices in the same computing environment 503. Additionally, it is understood that terms such as "application," "service," "system," "engine," "module," and so on may be interchangeable and are not intended to be limiting.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

Therefore, the following is claimed:
1. A refrigerator, comprising:
a computing device that comprises a processor and a memory;
a compartment having an interior space configured to contain a food item;
a chemical sensor mounted within an interior of the refrigerator and configured to at least measure an amount of a chemical related to spoilage of the food item in the compartment; and an application stored in the memory that, when executed by the processor, causes the computing device to at least determine that the amount of the chemical related to the spoilage of the food item exceeds a chemical threshold, the chemical threshold is based at least in part on an airflow rate associated with the compartment of the refrigerator.

2. The refrigerator of claim 1, wherein the chemical sensor is further configured to at least report the amount of the chemical related to the spoilage of the food item to a remote computing device.

3. The refrigerator of claim 1, wherein the refrigerator further comprises a network interface configured to report the amount of the chemical related to the spoilage of the food item to a remote computing device.

4. The refrigerator of claim 1, further comprising a camera configured to capture an image of the compartment.

5. The refrigerator of claim 4, wherein the camera comprises an infrared camera.

6. The refrigerator of claim 1,
wherein the application, when executed by the processor, causes the computing device to at least:
determine a measurement interval for the chemical sensor to take a plurality of measurements based at least in part on at least one of: an internal temperature of the refrigerator or the airflow rate for the compartment in the refrigerator.

7. The refrigerator of claim 1,
wherein the
chemical threshold associated with a spoilage indication is further determined based at least in part on a quantity of food items in the compartment.

8. The refrigerator of claim 1, wherein the compartment comprises a first compartment that is connected to a first airflow spine of the refrigerator, and further comprising:
a second compartment that is connected to a second airflow spine of the refrigerator, wherein the second airflow spine has an airflow that is isolated from the first airflow spine of the first compartment.

9. A refrigerator, comprising:
a computing device that comprises a processor and a memory;
a compartment having an interior space configured to contain a food item;
a chemical sensor mounted within an interior of the refrigerator; and
an application stored in the memory that, when executed by the processor, causes the processor to at least:
determine a threshold amount based at least in part on an airflow rate associated with the compartment;
perform, via the chemical sensor, a measurement of an amount of a chemical related to spoilage of the food item in the compartment; and
determine that the amount of the chemical related to the spoilage of the food item exceeds the threshold amount.

10. The refrigerator of claim 9, wherein the application, when executed by the processor, further causes the processor to at least:
determine a measurement interval for the chemical sensor to take a plurality of measurements based at least in part on at least one of: an internal temperature of the refrigerator or an amount of airflow in the refrigerator.

11. The refrigerator of claim 10, wherein the application, when executed by the processor, further causes the processor to at least:
compare the amount of airflow in the refrigerator and an expected airflow in the refrigerator as indicated in a refrigerator profile.

12. The refrigerator of claim 9, wherein the application, when executed by the processor, further causes the processor to at least:
determine the threshold amount associated with a spoilage indication based at least in part on a quantity of food items in the compartment.

13. The refrigerator of claim 9, wherein the chemical sensor comprises a network interface and is further configured to at least report the amount of the chemical related to the spoilage of the food item to a remote computing device.

14. A refrigerator, comprising:
a chemical sensor mounted within an interior of the refrigerator; and
a computing device that comprises a processor and a memory, wherein the processor is configured to at least:
determine a presence of a food item in an interior space of a compartment of the refrigerator;
determine a threshold amount based at least in part on an airflow rate associated with the compartment of the refrigerator;
cause the chemical sensor to measure an amount of a chemical related to spoilage of the food item; and
determine that the amount of the chemical related to the spoilage of the food item exceeds the threshold amount.

15. The refrigerator of claim 14, wherein the processor is further configured to at least:
determine the threshold amount based at least in part on a quantity of food items in the compartment or a volume size of the compartment.

16. The refrigerator of claim 15, wherein the processor is further configured to at least:
adjust the threshold amount for the compartment based at least in part on a change in the quantity of food items in the compartment.

17. The refrigerator of claim 14, wherein the processor is further configured to at least:
determine a measurement interval for the chemical sensor to take a plurality of measurements based at least in part on at least one of: an internal temperature of the refrigerator or an amount of airflow in the refrigerator.

18. The refrigerator of claim 14, wherein the processor is further configured to at least:
determine a measurement interval for the chemical sensor to take a plurality of measurements based at least in part on a comparison between an amount of airflow in the refrigerator and an expected airflow for the refrigerator.

* * * * *